United States Patent
Suigetsu et al.

(10) Patent No.: US 10,383,608 B2
(45) Date of Patent: Aug. 20, 2019

(54) JOINING STRUCTURE AND BIOPSY NEEDLE

(71) Applicant: OLYMPUS CORPORATION, Hachioji-shi, Tokyo (JP)

(72) Inventors: Naoki Suigetsu, Kokubunji (JP); Chie Hosoda, Nishitokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 176 days.

(21) Appl. No.: 15/359,874

(22) Filed: Nov. 23, 2016

(65) Prior Publication Data

US 2017/0071584 A1 Mar. 16, 2017

Related U.S. Application Data

(63) Continuation of application No. PCT/JP2015/066062, filed on Jun. 3, 2015.

(30) Foreign Application Priority Data

Jun. 4, 2014 (JP) .................................. 2014-116302

(51) Int. Cl.
  *B23K 1/00* (2006.01)
  *B23K 1/18* (2006.01)
  (Continued)

(52) U.S. Cl.
  CPC ................ *A61B 10/04* (2013.01); *B23K 1/00* (2013.01); *B23K 1/18* (2013.01); *B23K 1/19* (2013.01);
  (Continued)

(58) Field of Classification Search
  CPC ... B23K 1/19; B23K 1/18; B23K 1/00; B23K 2101/06; B23K 2103/24; B23K 2103/14;
  (Continued)

(56) References Cited

U.S. PATENT DOCUMENTS 3,205,573 A * 9/1965 Seal ...................... B23K 35/002
  228/132
3,791,026 A * 2/1974 Dufrene ............. B23K 35/3033
  228/154
(Continued)

FOREIGN PATENT DOCUMENTS

JP 51032453 A 3/1976
JP 04089149 A 3/1992
(Continued)

OTHER PUBLICATIONS

International Search Report (ISR) and Written Opinion dated Aug. 25, 2015 issued in International Application No. PCT/JP2015/066062.

*Primary Examiner* — Sean P Dougherty
(74) *Attorney, Agent, or Firm* — Holtz, Holtz & Volek PC (57) ABSTRACT

A joining structure includes: a first tube made of a first metal or alloy; a second tube made of a second metal or alloy different from the first metal or alloy; a coupling member having a cylindrical shape to provide therein a passage into which the first and second tubes are insertable, and having an opening on a side face thereof to penetrate into the passage; and a brazing material injected into the passage through the opening with an end face of the first tube and an end face of the second tube abutting on each other in the passage to braze the first tube, the second tube, and the coupling member. The second metal or alloy is more easily oxidizable than the first metal or alloy during brazing. An abutting position between the first and second tubes is deviated from the opening toward the second tube.

14 Claims, 6 Drawing Sheets (51) Int. Cl.
*B23K 1/19* (2006.01)
*A61B 10/04* (2006.01)
*B23K 101/06* (2006.01)
*B23K 103/04* (2006.01)
*B23K 103/14* (2006.01)
*B23K 103/24* (2006.01)

(52) U.S. Cl.
CPC ..... *A61B 2010/045* (2013.01); *B23K 2101/06* (2018.08); *B23K 2103/05* (2018.08); *B23K 2103/14* (2018.08); *B23K 2103/24* (2018.08)

(58) Field of Classification Search
CPC ............. B23K 2103/05; A61B 10/04; A61B 2010/045
See application file for complete search history.

(56) References Cited

U.S. PATENT DOCUMENTS

| | | | | |
|---|---|---|---|---|
| 4,084,842 A * | 4/1978 | Stonitsch | ............... | F16L 59/18 285/123.17 |
| 5,354,623 A * | 10/1994 | Hall | ............... | B23K 35/004 228/207 |
| 5,919,205 A * | 7/1999 | Heimberger | ............... | A61B 17/29 606/167 |
| 6,428,557 B1 * | 8/2002 | Hilaire | ............... | A61B 17/12022 606/200 |
| 6,514,631 B1 | 2/2003 | Yamamoto et al. | | |
| 8,220,695 B1 * | 7/2012 | Wei | ............... | B23K 1/0008 228/122.1 |
| 2002/0049392 A1 * | 4/2002 | DeMello | ............... | A61M 25/09 600/585 |
| 2004/0111020 A1 * | 6/2004 | Long | ............... | A61B 1/00133 600/407 |
| 2004/0193073 A1 * | 9/2004 | DeMello | ............... | A61M 25/09 600/585 |
| 2004/0236345 A1 * | 11/2004 | Greenberg | ............... | A61B 17/221 606/108 |
| 2005/0049612 A1 * | 3/2005 | Urbanski | ............... | A61B 17/221 606/127 |
| 2005/0227105 A1 * | 10/2005 | Jiang | ............... | A61N 1/372 428/660 |
| 2005/0263568 A1 * | 12/2005 | Stol | ............... | B23K 20/085 228/107 |
| 2006/0189891 A1 | 8/2006 | Waxman et al. | | |
| 2007/0100285 A1 * | 5/2007 | Griffin | ............... | A61M 25/0013 604/164.11 |
| 2007/0282270 A1 * | 12/2007 | Mathews | ............... | A61M 25/09 604/164.13 |
| 2011/0160680 A1 * | 6/2011 | Cage | ............... | A61M 25/09033 604/265 |
| 2013/0245376 A1 * | 9/2013 | Oku | ............... | A61B 1/00071 600/129 |
| 2013/0319569 A1 * | 12/2013 | Kikuno | ............... | B23K 1/0012 138/109 |

FOREIGN PATENT DOCUMENTS

| | | | |
|---|---|---|---|
| JP | 08061785 A | * | 3/1996 |
| JP | 11209850 A | | 8/1999 |
| JP | 2008523909 A | | 7/2008 |
| WO | 2006065913 A1 | | 6/2006 |

* cited by examiner

JOINING STRUCTURE AND BIOPSY NEEDLE

CROSS-REFERENCE TO RELATED APPLICATION

This application is a continuation of PCT international application Ser. No. PCT/JP2015/066062 filed on Jun. 3, 2015 which designates the United States, incorporated herein by reference, and which claims the benefit of priority from Japanese Patent Application No. 2014-116302, filed on Jun. 4, 2014, incorporated herein by reference.

BACKGROUND

1. Technical Field

The disclosure relates to a joining structure for joining tubes made of different kinds of metal or alloy. The disclosure also relates to a biopsy needle to which the joining structure is applied.

2. Related Art

There is known a biopsy needle as a treatment tool for collecting a cell or tissue in a living body. The biopsy needle has a cylindrical shape having a hollow space and collects a cell or tissue by puncturing a living body with the distal end portion thereof. There is also known a biopsy needle used as a treatment tool in an endoscope system which observes the inside of the lumen of a living body. Such a biopsy needle is inserted into the lumen through a treatment tool channel which is formed in an insertion unit of an endoscope to collect a cell or tissue of the wall surface.

The biopsy needle used in the endoscope system has a substantially linear shape, and includes a tubular needle which has a distal end portion capable of puncturing a living body, a needle tube which extends from the needle, and a tubular member into which the needle and the needle tube is insertable. In a conventional biopsy needle, the needle and the needle tube are integrally formed of, for example, stainless steel (SUS).

On the other hand, in recent years, a biopsy needle that includes a needle formed of a nickel-titanium (NiTi) alloy has also been put to practical use. A nickel-titanium alloy has an extremely high elastic function which is also called a superelastic function. Thus, a nickel-titanium alloy is flexibly deformed in response to an external force and substantially completely restored when the external force is eliminated. Thus, when a needle is formed of a nickel-titanium alloy, it is possible to easily move the needle forward and backward even with respect to a passage which is curved in a complicated manner.

If a needle and a needle tube are formed of different materials, there is known a technique in which the needle and the needle tube are inserted into a sleeve-shaped coupling member which is made of, for example, stainless steel (SUS), causes the distal end faces of the needle and the needle tube to abut on each other, and joins the needle, the needle tube, and the coupling member to one another with a brazing material or an adhesive (refer to WO 2006/065913 A, for example).

SUMMARY

In some embodiments, a joining structure includes: a first tube made of a first metal or alloy; a second tube made of a second metal or alloy different from the first metal or alloy; a coupling member having a cylindrical shape to provide therein a passage into which the first tube and the second tube are insertable, the coupling member having an opening on a side face thereof to penetrate from outside the coupling member to the passage; and a brazing material injected into the passage through the opening with an end face of the first tube and an end face of the second tube abutting on each other in the passage to braze the first tube, the second tube, and the coupling member. The second metal or alloy is more easily oxidizable than the first metal or alloy during brazing using the brazing material. An abutting position between the first tube and the second tube is deviated from the opening toward the second tube in an extending direction of the first tube and the second tube.

In some embodiments, a biopsy needle includes a joining structure. The joining structure includes: a first tube made of a first metal or alloy; a second tube made of a second metal or alloy different from the first metal or alloy; a coupling member having a cylindrical shape to provide therein a passage into which the first tube and the second tube are insertable, the coupling member having an opening on a side face thereof to penetrate from outside the coupling member to the passage; and a brazing material injected into the passage through the opening with an end face of the first tube and an end face of the second tube abutting on each other in the passage to braze the first tube, the second tube, and the coupling member. The second metal or alloy is more easily oxidizable than the first metal or alloy during brazing using the brazing material. An abutting position between the first tube and the second tube is deviated from the opening toward the second tube in an extending direction of the first tube and the second tube. A distal end portion of the second tube has a needle shape.

The above and other features, advantages and technical and industrial significance of this invention will be better understood by reading the following detailed description of presently preferred embodiments of the invention, when considered in connection with the accompanying drawings.

DETAILED DESCRIPTION

Hereinbelow, a joining structure and a biopsy needle according to some embodiments of the present invention will be described with reference to the drawings. The present invention is not limited to the embodiments. In the following embodiments, a biopsy needle is described as an example of a treatment tool used in a medical endoscope system which captures an intraluminal image of a subject such as a patient and displays the captured image. However, the present invention is not limited to the embodiments. The same reference signs are used to designate the same elements throughout the drawings. It is to be noted that the drawings are schematic drawings, and the relationship between the thickness and the width in each member and the ratio of each member may differ from the actual relationship and ratio. The dimension and the ratio may partially differ from each other also between the drawings.

Embodiments

Figure 1:
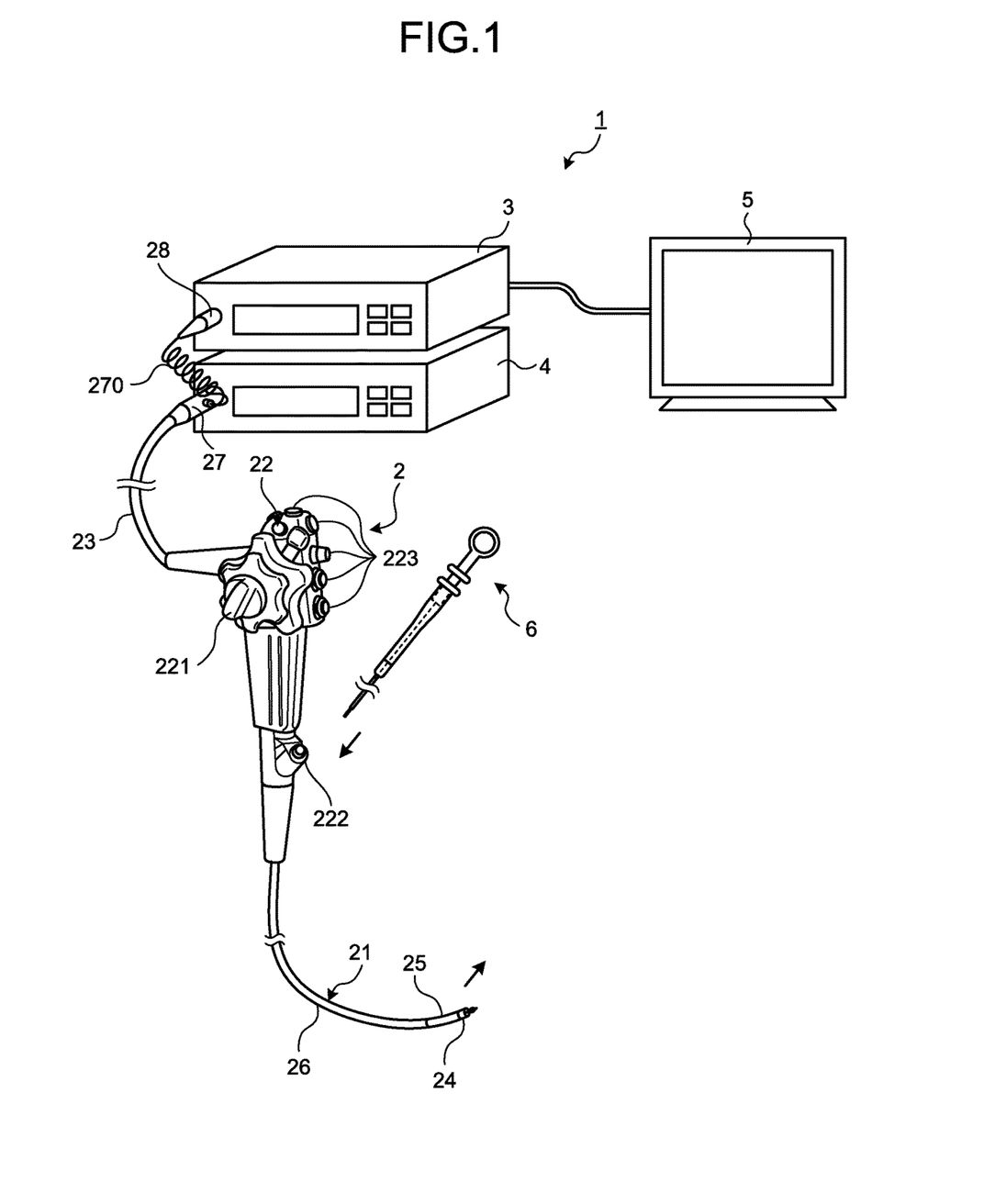
FIG. 1 is a diagram illustrating a schematic configuration of an endoscope system according to an embodiment of the present invention.

FIG. 1 is a diagram illustrating a schematic configuration of an endoscope system 1 according to an embodiment of the present invention. As illustrated in FIG. 1, the endoscope system 1 is provided with an endoscope 2 which images the inside of the body of a subject to generate an image by inserting a distal end unit thereof into the lumen of the subject, a control device 3 which applies predetermined image processing to the image generated by the endoscope 2 and totally controls the operation of the entire endoscope system 1, a light source device 4 which generates illumination light emitted from the distal end of the endoscope 2, a display device 5 which displays the in-vivo image image-processed by the control device 3, and a biopsy needle 6 as an example of a treatment tool which includes, on the distal end thereof, a functional member having an end effect, and is inserted into the endoscope 2 and exposed from the distal end of a distal end unit 24.

The endoscope 2 is provided with an insertion unit 21 which has flexibility and an elongated shape, an operating unit 22 which is connected to the proximal end of the insertion unit 21 and receives the input of various operation signals, and a universal cord 23 which extends from the operating unit 22 in a direction different from the extending direction of the insertion unit 21 and includes various built-in cables connected to the control device 3 and the light source device 4.

The insertion unit 21 includes the distal end unit 24 which has a built-in image sensor, a bendable unit 25 which includes a plurality of bending pieces so as to be bendable, and a flexible needle tube 26 which is connected to the proximal end of the bendable unit 25 and has a long shape.

The image sensor receives light from the outside, photoelectrically converts the received light to an electric signal, and performs predetermined signal processing on the electric signal. The image sensor is achieved by using, for example, a charge coupled device (CCD) image sensor or a complementary metal-oxide semiconductor (CMOS) image sensor.

A cable assembly is connected between the operating unit 22 and the distal end unit 24, the cable assembly including a bundle of signal lines which performs transmission and reception of an electric signal with the control device 3. The signal lines include a signal line for transferring a video signal output from the image sensor to the control device 3 and a signal line for transferring a control signal output from the control device 3 to the image sensor.

The operating unit 22 includes a bending knob 221 which bends the bendable unit 25 in the up-down and right-left directions, a treatment tool insertion unit 222 through which treatment tools such as, in addition to the biopsy needle 6, a biopsy forceps, a laser scalpel, and an inspection probe are inserted, and a plurality of switches 223 as an operation input unit which inputs operation instruction signals of peripheral devices such as an air feeding unit, a water feeding unit, and a gas feeding unit in addition to the control device 3 and the light source device 4.

The universal cord 23 incorporates therein at least a light guide and a cable assembly. On an end of the universal cord 23 opposite to where the operating unit 22 is provided, disposed are a connector 27 which is attachable to and detachable from the light source device 4, and an electric connector 28 which is electrically connected to the connector 27 through a coil cable 270 having a coil shape and attachable to and detachable from the control device 3.

The control device 3 generates an in-vivo image to be displayed by the display device 5 on the basis of an image signal output from the distal end unit 24. The control device 3 performs, for example, white balance (WB) adjustment, gain adjustment, gamma ($\gamma$) correction, D/A conversion, and format change.

The light source device 4 is provided with, for example, a light source, a rotary filter, and a light source controller. The light source is configured using, for example, a white light emitting diode (LED) or a xenon lamp and generates white light under the control of the light source controller. The light generated by the light source is applied from the distal end of the distal end unit 24 through the light guide.

The display device 5 has a function of receiving, from the control device 3, an in-vivo image generated by the control device 3 through a video cable and displaying the received in-vivo image. The display device 5 is configured using, for example, a liquid crystal or an organic electro luminescence (EL).

Figure 2:
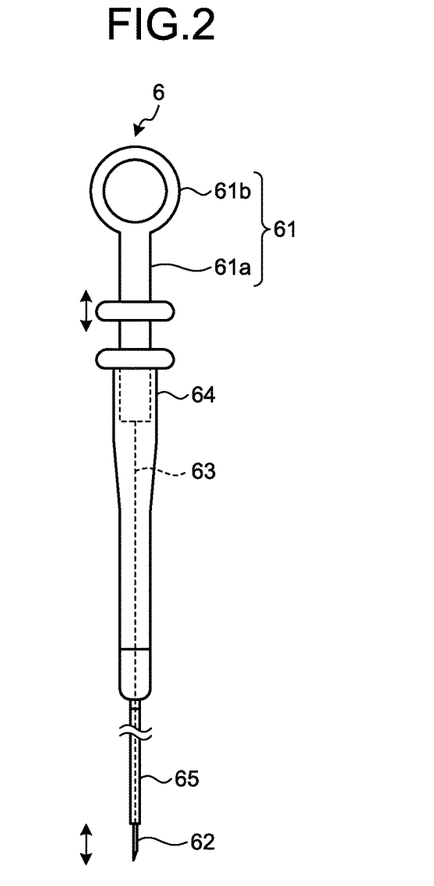
FIG. 2 is a schematic diagram describing a schematic configuration of a biopsy needle which is an example of a treatment tool illustrated in FIG. 1.
Figure 3:
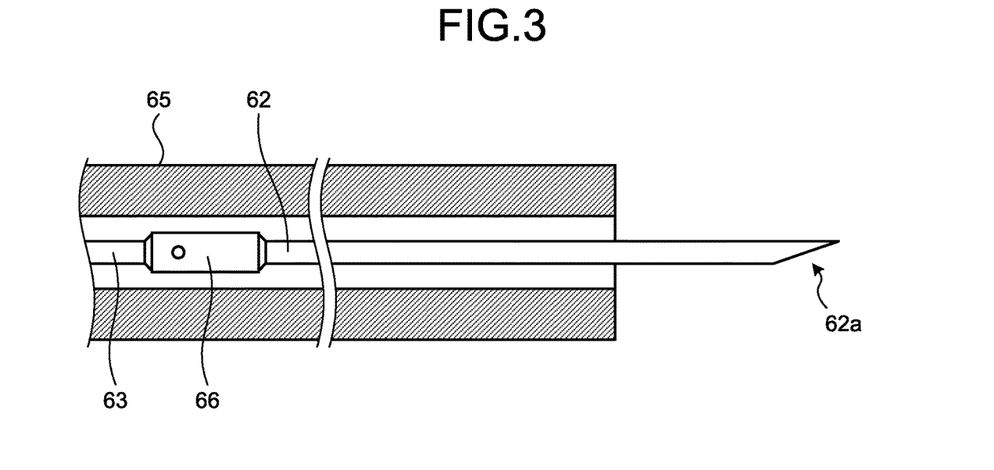
FIG. 3 is a partial sectional view illustrating a distal end portion of the biopsy needle illustrated in FIG. 2 and the vicinity thereof.

FIG. 2 is a schematic diagram illustrating a schematic configuration of the biopsy needle 6 illustrated in FIG. 1. FIG. 3 is a partial sectional view illustrating the distal end portion of the biopsy needle 6 and the vicinity thereof. In FIG. 3, only a flexible needle tube 65 (described below) is illustrated as a sectional view.

The biopsy needle 6 is provided with a holding member 61 which includes a base portion 61a having a substantially columnar shape and a holding portion 61b which is formed at the end of the base portion 61a and has an opening penetrating the holding portion 61b in a direction perpendicular to the longitudinal direction of the base portion 61a, a needle (second tube) 62 which is a functional unit whose distal end is formed in a needle shape, a needle tube (first tube) 63 which couples the holding member 61 and the needle 62 to each other, is bendable, and has a tubular shape, a housing 64 which has a substantially cylindrical shape and accommodates the base portion 61a and the needle tube 63 in a movable manner, and a flexible needle tube 65 which has a tubular shape and is disposed on an end of the housing 64 opposite to where the base portion 61a is accommodated. The needle 62 and the needle tube 63 with their end faces joined to each other is inserted in the flexible needle tube 65. In the endoscope 2, the flexible needle tube 65 is inserted from the treatment tool insertion unit 222, and the distal end of the flexible needle tube 65 is exposable from the distal end unit 24.

The needle 62 is formed using a tubular member which is made of a superelastic alloy typified by a nickel-titanium (NiTi) alloy. Although, the dimension of each portion of the needle 62 is not particularly limited to a specific dimension, for example, the outer diameter is approximately 0.5 to 1.3 mm and the inner diameter is approximately 0.3 to 1.2 mm. A distal end portion 62a of the needle 62 has a needle shape capable of puncturing a biological tissue. The needle 62 is exposable to the outside from the distal end of the flexible needle tube 65 in response to a reciprocating motion of the holding member 61 with respect to the housing 64.

The needle tube 63 is made of stainless steel such as SUS and formed using a tubular member whose outer diameter and inner diameter are equal to the outer diameter and the inner diameter of the needle 62. As illustrated in FIG. 3, the needle tube 63 is joined to the end of the needle 62 by, for example, brazing typified by soldering using a sleeve-like coupling member 66 which is made of stainless steel such as SUS.

The housing 64 forms a hollow space having a stepped shape. The hollow space of the housing 64 has a diameter that enables the insertion of the base portion 61a at one end side and has a diameter that enables the insertion of the needle 62 and the needle tube 63 at the other end side.

Figure 4:
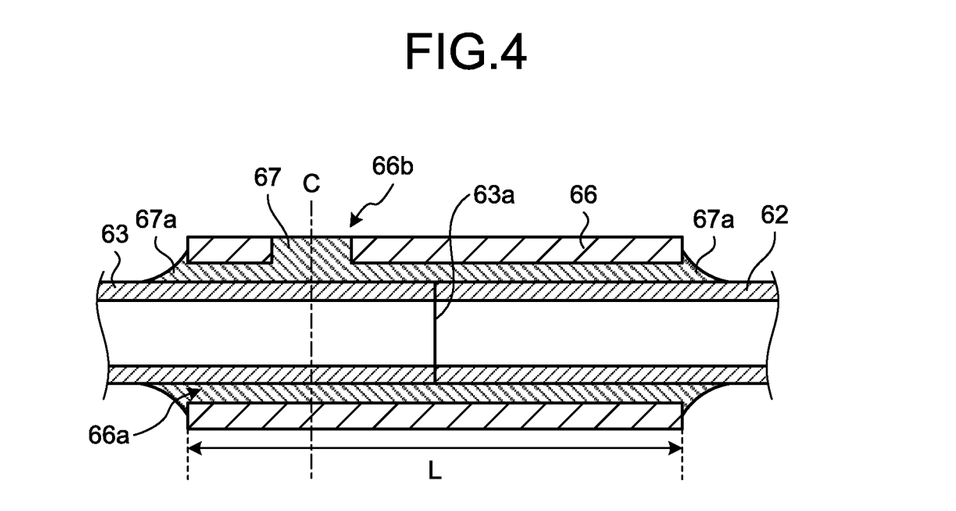
FIG. 4 is a sectional view illustrating a joining structure according to the embodiment of the present invention.
Figure 5:
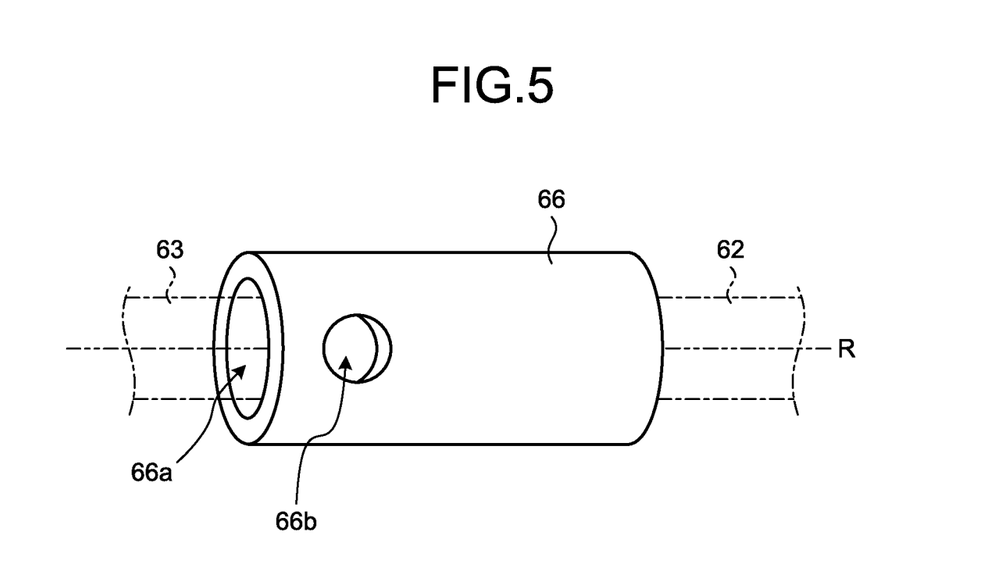
FIG. 5 is a perspective view illustrating the appearance of a coupling member illustrated in FIG. 4.

FIG. 4 is a sectional view illustrating a joining structure according to the embodiment and illustrating a state in which the needle 62 and the needle tube 63 are joined to each other using the coupling member 66. FIG. 5 is a perspective view illustrating the appearance of the coupling member 66.

The coupling member 66 has a cylindrical shape to provide therein a passage 66a into which the needle 62 and the needle tube 63 are insertable. The outer diameter of the coupling member 66 is not particularly limited to a specific diameter as long as the coupling member 66 is insertable into the flexible needle tube 65. The inner diameter of the coupling member 66 is set in such a manner that a clearance between the inner peripheral face of the coupling member 66 and the outer peripheral faces of the needle 62 and the needle tube 63 is, for example, approximately 0.02 to 0.2 mm.

An opening is formed on the side face of the coupling member 66 and penetrates the coupling member 66 from the outside through the passage 66a. Hereinbelow, the opening is referred to as a through hole 66b. In the embodiment, the through hole 66b is located deviating from the center of the cylindrical coupling member 66 in the height direction, that is, in the direction of the central axis R. Preferably, the center C of the through hole 66b is deviated from the center of the coupling member 66 in the height direction by approximately a quarter of the length L of the coupling member 66.

As described below, the diameter of the through hole 66b is not particularly limited to a specific diameter as long as a molten brazing material can be injected into the passage 66a.

The needle 62 and the needle tube 63 are joined to the coupling member 66 with their end faces abutting on each other inside the passage 66a of the coupling member 66 with a brazing material 67, for example, solder. In the embodiment, the needle 62 and the needle tube 63 abut on each other at substantially the center of the coupling member 66 in the direction of the central axis R. Thus, the abutting position between the needle 62 and the needle tube 63, that is, the position of an abutting surface 63a is deviated from the through hole 66b of the coupling member 66 toward the needle 62 in the extending direction of the needle 62 and the needle tube 63. Accordingly, the through hole 66b faces the outer peripheral face of the needle tube 63.

The brazing material 67 is molten by heating, and the molten brazing material 67 is injected into the passage 66a through the through hole 66b so as to be filled in the passage 66a and the through hole 66b to join the needle 62, the needle tube 63, and the coupling member 66 to each other. The brazing material 67 wetly spreads inside the passage 66a and reaches both ends of the coupling member 66 to form a fillet 67a therein. The kind of the brazing material 67 is not particularly limited to a specific kind as long as the needle 62, the needle tube 63, and the coupling member 66 can be joined to each other. As an example, when the needle 62 made of a nickel-titanium alloy, the needle tube 63 made of stainless steel, and the coupling member 66 are joined, Sn—Ag—Cu solder or Sn—Ag solder is preferably used.

Figure 6:
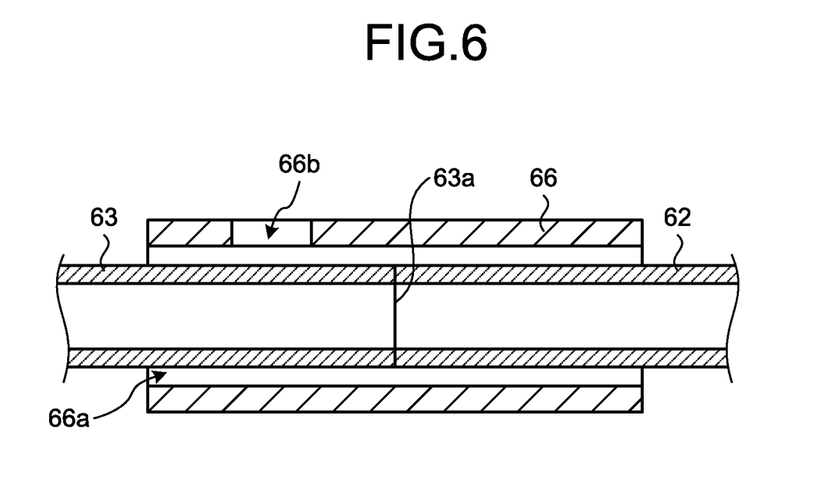
FIG. 6 is a sectional view for describing a joining method according to the embodiment of the present invention.

Next, a joining method according to the embodiment will be described. FIG. 6 is a sectional view for describing the joining method according to the embodiment.

First, as illustrated in FIG. 6, the needle 62 and the needle tube 63 are inserted into the passage 66a of the coupling member 66, and the end face of the needle 62 and the end face of the needle tube 63 abut on each other. At this time, the abutting position is adjusted such that the needle tube 63 is located where the through hole 66b is located, and the needle 62 and the needle tube 63 abut on each other at a position deviating from the through hole 66b toward the needle 62. In the embodiment, since the through hole 66b is deviated from the center of the coupling member 66 toward one end thereof, the abutting surface 63a may be located at substantially the center of the coupling member 66.

Then, the brazing material 67 is molten by heating and injected into the passage 66a through the through hole 66b so as to be filled in a gap between the needle 62 and the coupling member 66 and between the needle tube 63 and the coupling member 66. At this time, a flux may be appropriately supplied. When it is confirmed that the fillet 67a (refer to FIG. 4) has been formed at both ends of the coupling member 66 and the brazing material 67 has been solidified, the joining is completed.

Figure 7:
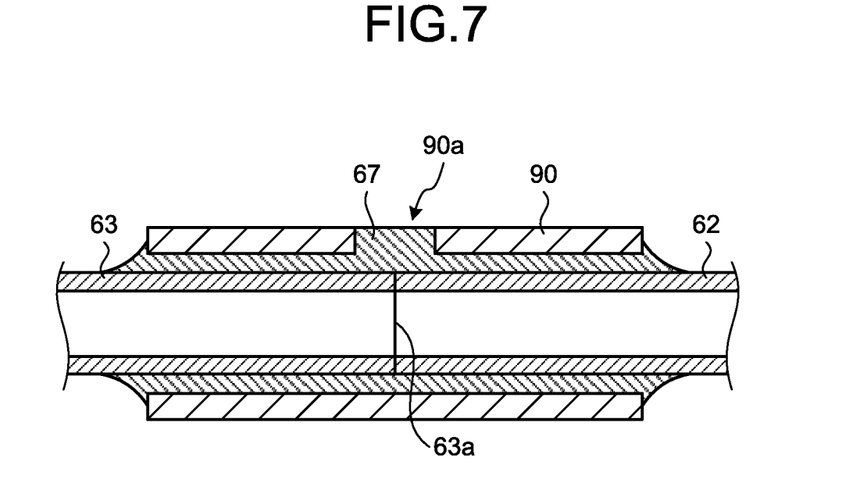
FIG. 7 is a reference diagram for explaining the reason why an abutting position between a needle and a needle tube is deviated from a through hole toward the needle.

Next, reference will be made to the reason why the needle 62 and the needle tube 63 abut on each other at a position deviating toward the needle 62 from the through hole 66b through which the brazing material 67 is injected. FIG. 7 is a reference diagram for explaining the reason.

As illustrated in FIG. 7, when the needle 62 and the needle tube 63 are brazed within a range where a through hole 90a formed on the side face of a coupling member 90 is open, the needle 62 is also heated when the brazing material 67 is molten and injected through the through hole 90a. A nickel-titanium alloy which forms the needle 62 is relatively easily oxidized. Thus, the surface of the needle 62 is oxidized by the heating during brazing. As a result, the wettability of the brazing material 67 is reduced, and a sufficient joining strength between the brazing material 67 and the needle 62 cannot be obtained.

In the embodiment, on the other hand, as illustrated in FIG. 4, the needle tube 63 made of stainless steel is disposed within a range where the through hole 66b is open. Thus, when the brazing material 67 is molten and injected through the through hole 66b, the needle 62 is less likely to be heated, which enables the oxidation of the needle 62 to be reduced. Accordingly, it is possible to ensure an excellent wettability of the brazing material 67 with respect to the surface of the needle 62 and firmly join the needle 62 and the brazing material 67 to each other. On the other hand, stainless steel is an alloy that is relatively less likely to be oxidized. Thus, even when the needle tube 63 is heated during the injection of the brazing material 67 through the through hole 66b, the surface of the needle tube 63 is not oxidized, and it is possible to ensure a sufficient joining strength between the needle tube 63 and the brazing material 67.

When the needle tube 63 is bent during the use or packaging of the biopsy needle 6, a bending stress may be applied to the abutting surface 63a between the needle 62 and the needle tube 63. In this case, when the abutting surface 63a between the needle 62 and the needle tube 63 is located within the range where the through hole 90a is open as illustrated in FIG. 7, stress concentration occurs at an intersection point between the abutting surface 63a and the interface of the brazing material 67. As a result, the brazing material 67 may be broken from the intersection point, which may reduce the airtightness between the needle 62 and the needle tube 63.

On the other hand, as illustrated in FIG. 4, when the abutting surface 63a between the needle 62 and the needle tube 63 is not aligned with the through hole 66b, the stress concentration at the intersection point between the abutting surface 63a and the interface of the brazing material 67 can be prevented. As a result, the joining strength between the needle 62 and the needle tube 63 can be stably ensured, and the airtightness between the needle 62 and the needle tube 63 can be maintained.

As described above, according to the embodiments, it is possible to firmly join the needle 62 and the needle tube 63 to each other and to stably maintain the joining strength. Thus, it is possible to ensure the airtightness between the needle 62 and the needle tube 63 to maintain the quality of the biopsy needle 6.

First Modification

Figure 8:
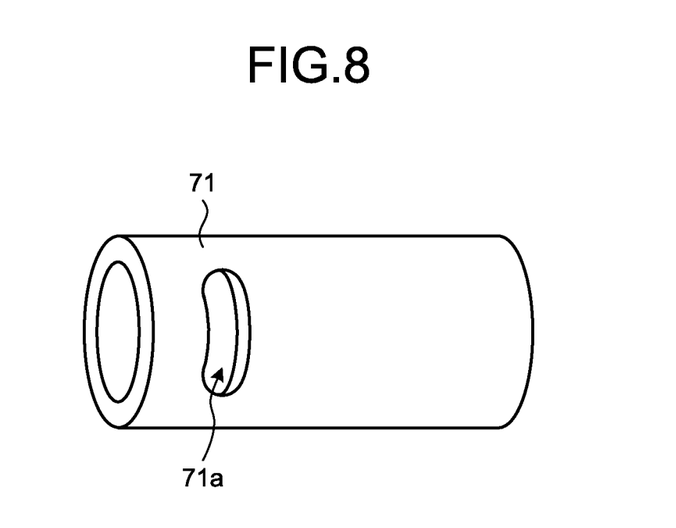
FIG. 8 is a perspective view illustrating the appearance of a coupling member in a first modification of the embodiment of the present invention.
Figure 9:
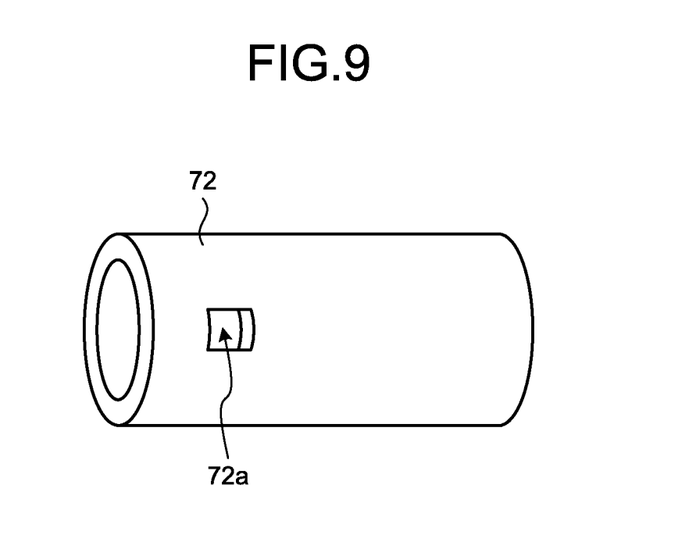
FIG. 9 is a perspective view illustrating the appearance of the coupling member in the first modification of the embodiment of the present invention.

Next, a first modification of the embodiment of the present invention will be described. FIGS. 8 and 9 are perspective views illustrating the appearance of a coupling member in the first modification. An end of the through hole for injecting a molten brazing material into the passage of the coupling member may have various shapes other than a circular shape. For example, there may be employed a coupling member 71 as illustrated in FIG. 8 which includes a through hole 71a whose end has a long hole shape, or a coupling member 72 as illustrated in FIG. 9 which includes a through hole 72a whose end has a rectangular shape. Alternatively, the end of the through hole may have an elliptical shape or a polygonal shape such as a hexagonal shape. For example, when a brazing material does not sufficiently spread in a gap between the needle 62 and the coupling member and between the needle tube 63 and the coupling member, such an end having a long hole shape or a rectangular shape enables the brazing material to be appropriately filled.

Second Modification

Figure 10:
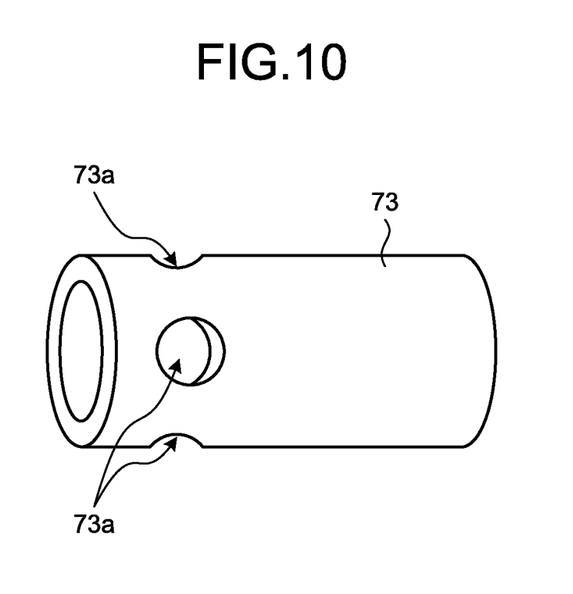
FIG. 10 is perspective view illustrating the appearance of a coupling member in a second modification of the embodiment of the present invention.

Next, a second modification of the embodiment of the present invention will be described. FIG. 10 is a perspective view illustrating the appearance of a coupling member in the second modification. The coupling member may be provided with a plurality of through holes for injecting a molten brazing material into the passage of the coupling member. For example, FIG. 10 illustrates an example in which a plurality of through holes 73a, each of which has a circular end, is formed on the same circumference of a circle perpendicular to the height direction (the central axis direction) of a coupling member 73 having a cylindrical shape.

When only one through hole is provided, it may be difficult for a brazing material injected through the through hole to spread to the back faces of the needle 62 and the needle tube 63 (refer to FIG. 4). Thus, it is possible to allow the brazing material to sufficiently spread throughout the outer peripheral faces of the needle 62 and the needle tube 63 to obtain a stable joint quality by providing the plurality of through holes 73a and injecting a brazing material through each of the through holes 73a.

Third Modification

Figure 11:
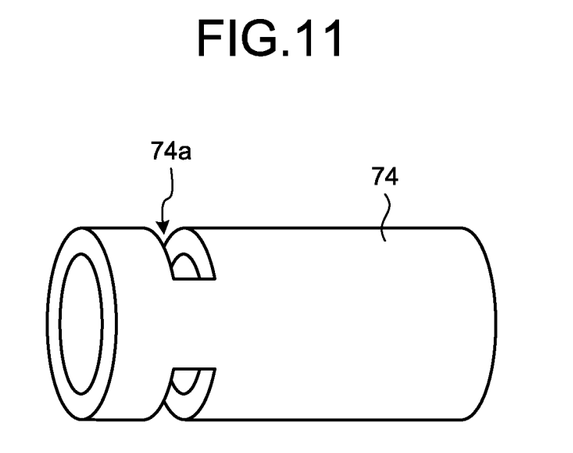
FIG. 11 is a perspective view illustrating the appearance of a coupling member in a third modification of the embodiment of the present invention.

Next, a third modification of the embodiment of the present invention will be described. FIG. 11 is a perspective view illustrating the appearance of a coupling member in the third modification. As illustrated in FIG. 11, a cut-away portion 74a may be provided instead of a through hole (e.g., the through hole 66b illustrated in FIG. 5) as an opening for injecting a molten brazing material into a coupling member 74. The cut-away portion 74a is formed by cutting away a part of the side face of a cylindrical member made of, for example, stainless steel.

In this case, it is possible to increase the opening area by increasing the opening width in the circumferential direction of the cylindrical coupling member 74 while maintaining the opening width in the height direction (the central axis direction) thereof substantially equal to that of the through hole 66b. Accordingly, the brazing material can be easily injected into the coupling member 74, and the brazing material can sufficiently spread throughout the outer peripheral faces of the needle 62 and the needle tube 63 inserted in the coupling member 74. Thus, it is possible to further reduce the number of injections of the brazing material or further reduce the injection time of the brazing material while reducing the heating of the needle 62. As a result, it is possible to more reliably join the needle 62, the needle tube 63, and the coupling member 74 to each other with the brazing material.

Although, in FIG. 11, the end of the cut-away portion 74a has a rectangular shape, the shape of the end is not particularly limited to a specific shape. The end of the cut-away portion 74a may have a curved shape such as a circular-arc shape.

Although, in the embodiments and the first to third modifications described above, joining of the needle 62 made of a nickel-titanium alloy and the needle tube 63 made of stainless steel is described, the present invention can be applied to any combination of materials such as metals or alloys having different degrees of easiness of oxidation.

The present invention described above is not limited to the embodiments and the first to third modifications, and can be modified in various manners according to, for example, specifications. For example, some of the components described in the embodiment and the first to third modifications may be eliminated. It is obvious from the above description that other various embodiments can be employed within the range of the present invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A joining structure comprising:
    a first tube made of a first metal or alloy;
    a second tube made of a second metal or alloy different from the first metal or alloy;
    a coupling member having a cylindrical shape and including a passage into which the first tube and the second tube are inserted such that an end face of the first tube and an end face of the second tube abut on each other, the coupling member having an opening in a side face thereof that penetrates from outside the coupling member to the passage; and a brazing material injected into the passage through the opening in a state in which the end face of the first tube and the end face of the second tube abut on each other in the passage, to braze the first tube, the second tube, and the coupling member, wherein:

the second metal or alloy is more easily oxidizable than the first metal or alloy during brazing using the brazing material, and the opening, the first tube, and the second tube are positioned with respect to each other such that the opening faces only the first tube made of the first metal or alloy.

2. The joining structure according to claim 1, wherein the first tube and the second tube abut on each other at a center in a central axis direction of the cylindrical shape of the coupling member.

3. The joining structure according to claim 1, further comprising one or more additional openings positioned, with respect to said opening, on a same circumference perpendicular to a central axis direction of the cylindrical shape of the coupling member.

4. The joining structure according to claim 1, wherein an end of the opening has a circular shape, an elliptical shape, a long hole shape, or a polygonal shape.

5. The joining structure according to claim 1, wherein the opening is formed by cutting away a part of the side face of the coupling member.

6. The joining structure according to claim 1, wherein the second metal or alloy includes a superelastic alloy.

7. The joining structure according to claim 6, wherein the first metal or alloy is stainless steel, and the second metal or alloy is a nickel-titanium alloy.

8. The joining structure according to claim 1, wherein:

an outer diameter of the first tube is equal to an outer diameter of the second tube, and an inner diameter of the first tube is equal to an inner diameter of the second tube.

9. The joining structure according to claim 1, wherein an inner diameter of the passage is greater than outer diameters of the first and second tubes.

10. The joining structure according to claim 9, wherein a clearance between an inner peripheral face of the passage and outer peripheral faces of the first and second tubes is in a range of from 0.02 to 0.2 mm.

11. The joining structure according to claim 1, wherein the brazing material fills a gap between an inner peripheral face of passage and outer peripheral faces of the first and second tubes.

12. The joining structure according to claim 1, wherein the brazing material surrounds outer peripheral faces of the first and second tubes.

13. The joining structure according to claim 1, wherein the brazing material forms fillets at both longitudinal ends of the coupling member.

14. A biopsy needle comprising a joining structure, the joining structure comprising:

a first tube made of a first metal or alloy;

a second tube made of a second metal or alloy different from the first metal or alloy;

a coupling member having a cylindrical shape and including a passage into which the first tube and the second tube are inserted such that an end face of the first tube and an end face of the second tube abut on each other, the coupling member having an opening in a side face thereof that penetrates from outside the coupling member to the passage; and a brazing material injected into the passage through the opening in a state in which the end face of the first tube and the end face of the second tube abut on each other in the passage, to braze the first tube, the second tube, and the coupling member, wherein:

the second metal or alloy is more easily oxidizable than the first metal or alloy during brazing using the brazing material, and the opening, the first tube, and the second tube are positioned with respect to each other such that the opening faces only the first tube made of the first metal or alloy, wherein a distal end portion of the second tube has a needle shape.

* * * * *